(12) United States Patent
Chung et al.

(10) Patent No.: US 9,947,359 B2
(45) Date of Patent: Apr. 17, 2018

(54) HOLOGRAPHIC CHARACTERIZATION AND PLAYBACK APPARATUS

(71) Applicant: GWANGJU INSTITUTE OF SCIENCE AND TECHNOLOGY, Gwangju (KR)

(72) Inventors: Euiheon Chung, Gwangju (KR); Tae Joong Eom, Gwangju (KR); Canghuei Yang, Pasadena, CA (US); Mooseok Jang, Pasadena, CA (US); Jihee Ryu, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 0 days.

(21) Appl. No.: 15/456,832

(22) Filed: Mar. 13, 2017

(65) Prior Publication Data
US 2017/0263281 A1  Sep. 14, 2017

(30) Foreign Application Priority Data

Mar. 11, 2016 (KR) .................. 10-2016-0029532

(51) Int. Cl.
| | | |
|---|---|---|
| G11B 7/0065 | (2006.01) |
| G11B 7/1353 | (2012.01) |
| G11B 7/128 | (2012.01) |
| G11B 7/13 | (2012.01) |
| G11B 7/1362 | (2012.01) |
| G11B 7/1374 | (2012.01) |
| G11B 7/1395 | (2012.01) |
| G01N 21/01 | (2006.01) |
| G01N 21/17 | (2006.01) |
| G01N 21/47 | (2006.01) |
| G03H 1/22 | (2006.01) |
| G03H 1/04 | (2006.01) |

(52) U.S. Cl.
CPC ........... *G11B 7/1353* (2013.01); *G01N 21/01* (2013.01); *G01N 21/17* (2013.01); *G01N 21/47* (2013.01); *G03H 1/041* (2013.01); *G03H 1/0443* (2013.01); *G03H 1/0465* (2013.01); *G03H 1/2205* (2013.01); *G11B 7/0065* (2013.01); *G11B 7/128* (2013.01); *G11B 7/13* (2013.01); *G11B 7/1362* (2013.01); *G11B 7/1374* (2013.01); *G11B 7/1395* (2013.01); *G03H 2001/2244* (2013.01); *G03H 2222/31* (2013.01); *G03H 2223/14* (2013.01); *G03H 2223/17* (2013.01); *G03H 2227/03* (2013.01)

(58) Field of Classification Search
None
See application file for complete search history.

(56) References Cited

U.S. PATENT DOCUMENTS

2006/0012845 A1* 1/2006 Edwards .............. G02B 5/0221
359/237

* cited by examiner

*Primary Examiner* — Brian Butcher
(74) *Attorney, Agent, or Firm* — Hauptman Ham, LLP

(57) ABSTRACT

A holographic characterization and playback apparatus is provided, which includes a light source, an optical path-forming optical system for separating the light emitted from the light source into a probe light and a reference light of different polarizations, and combining optical paths of the probe light and the reference light.

16 Claims, 8 Drawing Sheets

HOLOGRAPHIC CHARACTERIZATION AND PLAYBACK APPARATUS

CROSS-REFERENCE TO RELATED APPLICATIONS

This application claims priority from Korean Patent Application No. 10-2016-0029532, filed on Mar. 11, 2016 in the Korean Intellectual Property Office, the disclosure of which is incorporated herein by reference in its entirety.

BACKGROUND

1. Field of the Invention

The present disclosure relates to a holographic characterization and playback apparatus, and more particularly, to a holographic characterization and playback apparatus in which a scattering lens is disposed on an optical path of a probe light.

2. Description of the Related Art

In holographic data storage, recording involves storing information in the form of interference fringes into a material such as a photopolymer that responds to the intensity of light. The interference fringes are formed by using two laser beams. That is, the interference fringe formed by interference between the reference light and the signal light is recorded by causing a chemical or physical change in the photosensitive storage medium. In order to play back the information from the interference fringes recorded in the above manner, reference light similar to the light used for recording is irradiated onto the interference fringes recorded on the storage medium. The irradiated reference light is diffracted by the interference fringe, whereby the signal light is restored and the information is played back.

The recording method using such hologram technologies includes a volume holography method for recording/playing back information on a page basis, and a microholography method for recording/playing back information with a single bit. Although the volume holography method has the advantage of processing a large amount of information simultaneously, it is difficult to commercialize it as an information storage device for use by the general consumers since it requires precision adjustment of an optical system.

On the other hand, the microholography method forms fine interference fringes by an interference of two focused light beams at a focal point, in which the interference fringes are recorded, while a position on a plane of the storage medium is moved thus forming layers and these layers are recorded and superposed in the depth direction of the storage medium so that the information is recorded three-dimensionally on the storage medium.

However, a general microholographic recording/reproducing device employs an optical system simply composed of a lens group such as a focusing lens and an objective lens, thus providing somewhat limited performance in 3D focusing and multi-focusing.

SUMMARY

The present disclosure has been made in order to solve the above problems, and it is an object of the present disclosure to provide a holographic characterization and playback apparatus, which is provided with a scattering lens disposed on an optical path of a probe light to scatter light focused from an objective lens.

According to the present invention for achieving the above object, a holographic characterization and playback apparatus is provided, which may include a light source for emitting light, an optical path-forming optical system for, in the characterization mode, separating the light emitted from the light source into a probe light and a reference light of different polarizations from each other and advancing the same, and then combining optical paths of the probe light and the reference light, an objective lens disposed on the optical path of the probe light to focus the probe light, and movable along an optical path direction of the probe light so as to vary a focal position of the probe light along a depth direction of a holographic data storage medium, a 4F system disposed on the optical path of the probe light between the objective lens and the holographic data storage medium to relay the probe light toward the holographic data storage medium, and a scattering lens disposed on the optical path of the probe light between the objective lens and the 4F system to scatter the probe light focused by the objective lens.

Moreover, the holographic characterization and playback apparatus according to the present invention may include a beam blocking part disposed on the optical path of the probe light between the light source and the objective lens to block the probe light in a playback mode, an optical modulator for, in the playback mode, receiving the reference light transferred through the optical path-forming optical system, modulating the reference light to emit a playback light, and emitting the playback light along the optical path of the probe light in a direction opposite an irradiation direction of the probe light, a photodetector disposed at a position adjacent to the optical path of the probe light to detect the playback light, and a beam splitter disposed on the optical path of the probe light in front of the objective lens with reference to an advancing direction of the probe light to pass the probe light entering the objective lens, while transferring the playback light that has passed through the objective lens to the photodetector.

The scattering lens may include a slide plate formed of a light transmitting material, and a scattering layer formed by applying scattering particles onto a surface of the slide plate so as to scatter light passing through the slide plate.

It is preferable that the scattering particles may include zinc oxide.

The optical path-forming optical system may include a first optical path converter for splitting the light emitted from the light source into the probe light and the reference light, first and second polarization parts respectively disposed on the optical paths of the probe light and the reference light separated from the first optical path converter, and converting polarized lights of the probe light and the reference light so as to include two mutually orthogonally polarized lights, a conversion mirror disposed on the optical path of the probe light that has passed through the first polarization part to change the optical path of the probe light to a direction intersecting with the optical path of the reference light, and a second optical path converter disposed at an intersection of the probe light whose optical path is changed by the conversion mirror and the reference light, to change optical path so that the probe light and the reference light are interfered with each other so as to be incident on the holographic data storage medium.

The optical path-forming optical system may further include a first filter member disposed on the optical path of the probe light between the first optical path converter and the first polarization part to filter the probe light.

The optical path-forming optical system further comprises a second filter member disposed on the optical path of the reference light between the first optical path converter and the second polarization part to filter the reference light.

The first polarization part may include a first focusing lens disposed on the optical path of the probe light behind the first optical path converter with reference to the irradiation direction of the probe light, and a first polarization conversion element disposed on the optical path of the probe light behind the first focusing lens to change a polarization state of the probe light that has passed through the first focusing lens.

The first polarization part may further include a first linear polarizer disposed on the optical path of the probe light behind the first polarization conversion element with reference to the irradiation direction of the probe light to convert the probe light that has passed through the first polarization conversion element into linearly polarized light.

The second polarization part may include a second focusing lens disposed on the optical path of the reference light behind the first optical path converter with reference to the irradiation direction of the reference light, and a second polarization conversion element disposed on the optical path of the reference light behind the second focusing lens to change the polarization state of the reference light that has passed through the second focusing lens.

The second polarization part may further include a second linear polarizer disposed on the optical path of the reference light behind the second polarization conversion element with reference to the irradiation direction of the reference light to convert the reference light that has passed through the second polarization conversion element into linearly polarized light.

The first and second focusing lenses may be formed with different focal distances from each other.

The first focusing lens may be formed with a focal distance of 30 mm, and the second focusing lens may be formed with a focal distance of 200 mm.

Meanwhile, the holographic characterization and playback apparatus in an embodiment may preferably further include a third linear polarizer disposed on the optical path of the probe light between the scattering lens and a 4F system to convert the probe light that has passed through the scattering lens into linearly polarized light.

The second optical path converter in a playback mode may reflect the reference light incident from the second polarization part toward the optical modulator, while passing the playback light so that the playback light emitted from the optical modulator is emitted along the optical path of the probe light.

The 4F system may include a plurality of third focusing lenses spaced apart from one another along the optical path of the probe light, and a transmissive plate disposed on the optical path of the probe light among the plurality of third focusing lenses, in which the transmissive plate may include an aperture formed on an optical axis of the probe light so that the probe light can pass through.

The holographic characterization and playback apparatus according to the exemplary embodiments of the present disclosure may include a scattering lens disposed on the optical path of the probe light so as to scatter the light focused from the objective lens, thereby providing advantages that it is possible to enhance the performance for 3D focusing and multi focusing of the apparatus.

BRIEF DESCRIPTION OF THE DRAWINGS

The above and/or other aspects of the present inventive concept will be more apparent by describing certain exemplary embodiments of the present inventive concept with reference to the accompanying drawings, in which.

DETAILED DESCRIPTION OF EXEMPLARY EMBODIMENTS

Figure 1:
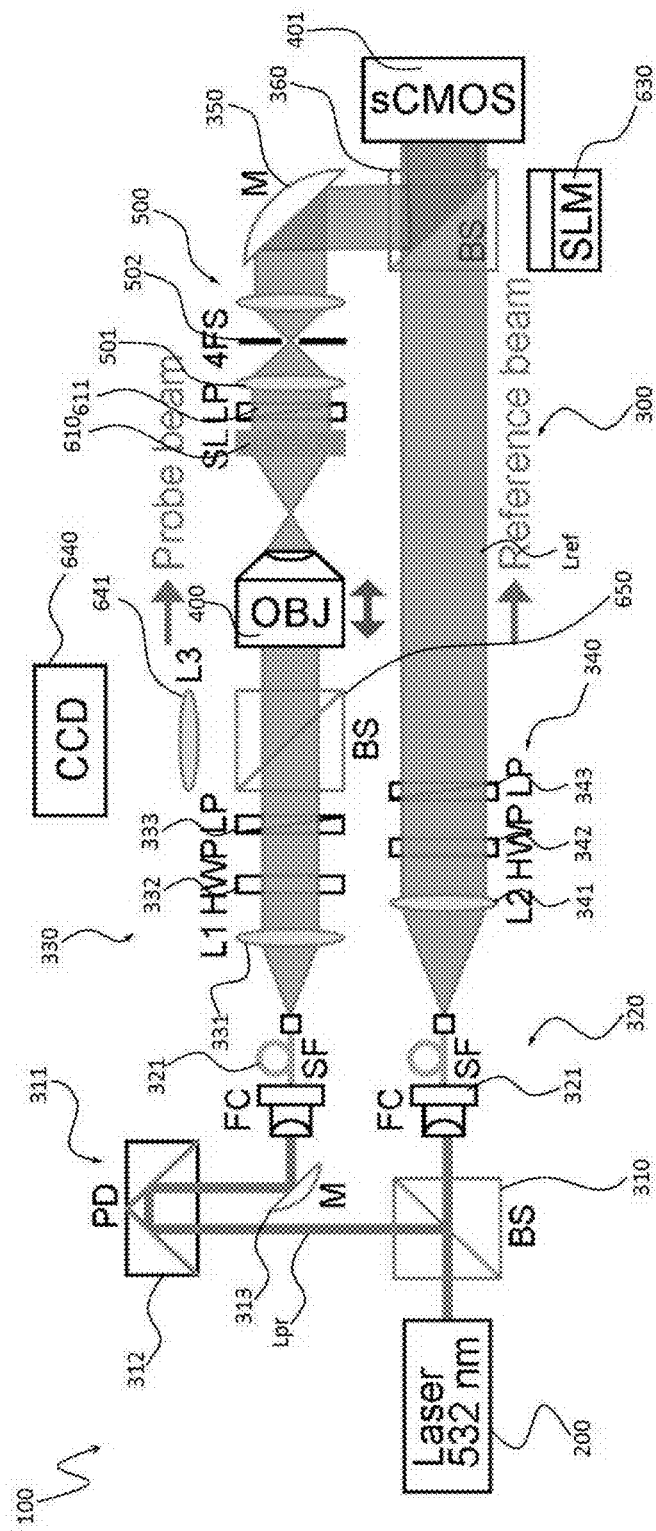
FIG. 1 is a schematic diagram of a characterization mode of a holographic characterization and playback apparatus according to exemplary embodiments.

Hereinafter, a holographic characterization and playback apparatus according to exemplary embodiments will be described in detail with reference to the accompanying drawings. Various modifications can be applied and various forms can be provided, in which specific embodiments are illustrated in the drawings and described herein in detail. It should be understood, however, that the invention is not intended to be limited to any particular embodiments disclosed herein, but on the contrary, is intended to cover all modifications, equivalents, and alternatives falling within the spirit and scope of the invention. Similar reference numerals refer to similar parts throughout the drawings. In the accompanying drawings, the dimensions of the structures are exaggerated for clarity of the present disclosure.

The terms "first," "second," etc. as used herein may be used to describe various elements, but the elements should not be limited by the terms. The terms are used only for the purpose of distinguishing one element from another. For example, without departing from the scope of the present disclosure, the first element may be referred to as a second element, and similarly, the second element may also be referred to as the first element.

The terminology used herein is for the purpose of describing particular embodiments only and is not intended to be limiting of the invention. A singular expression includes a plural expression unless the context clearly dictates otherwise. It is to be understood herein that the terms "comprise," "have,", and the like are intended to designate the presence of characteristics, numbers, steps, operations, elements, parts or combinations thereof, but do not preclude the presence or addition of one or more characteristics, numbers, steps, operations, elements, parts, or combinations thereof.

Unless otherwise defined, all terms used herein, including technical or scientific terms, have the same meaning as commonly understood by one of ordinary skill in the art to which this invention pertains. Terms such as those defined in commonly used dictionaries are to be interpreted as having a meaning consistent with the contextual meaning of the related art and not interpreted as an ideal or overly formal sense unless explicitly defined in the present application.

Figure 2:
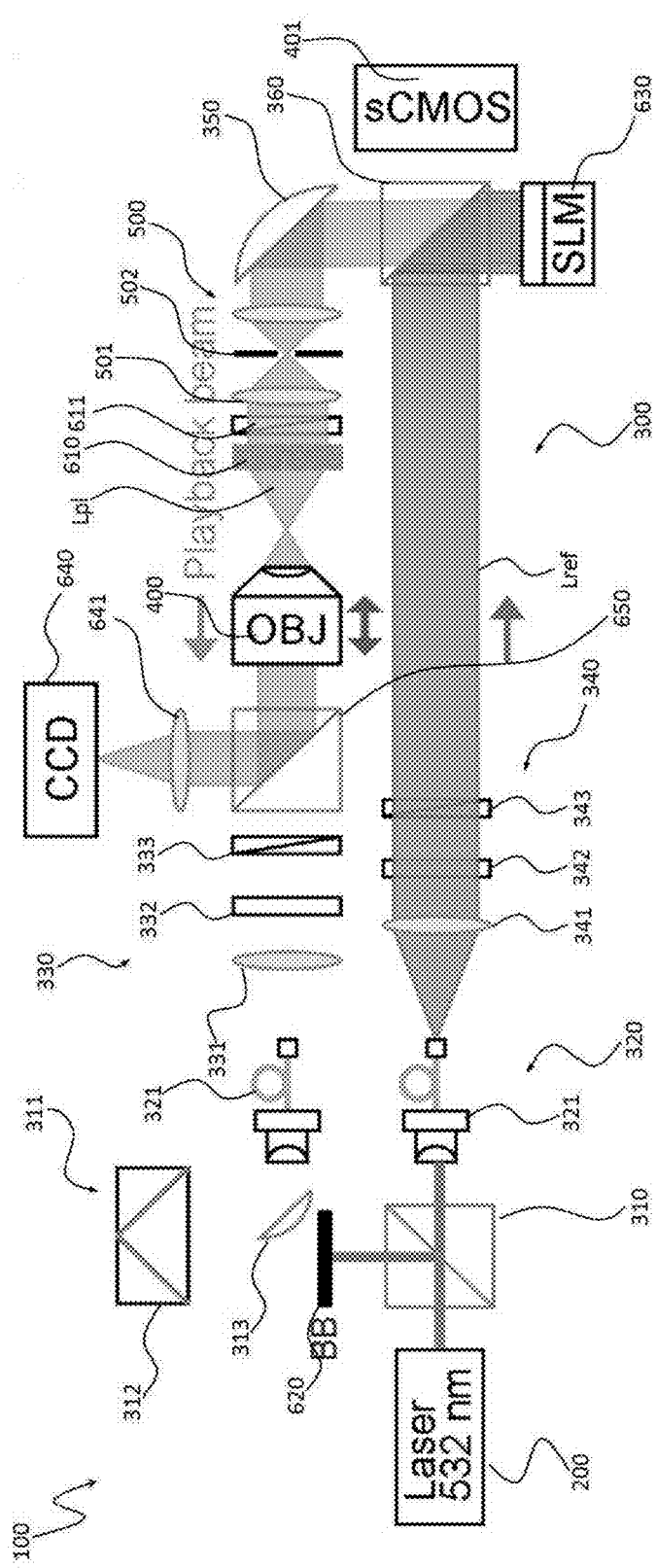
FIG. 2 is a schematic diagram of a playback mode of a holographic characterization and playback apparatus according to exemplary embodiments.

FIGS. 1 and 2 illustrate an operating state of a holographic characterization and playback apparatus 100 in a characterization mode and a playback mode.

Referring to the drawings, the holographic characterization and playback apparatus 100 includes a light source 200 for emitting light, an optical path-forming optical system 300 for, in the characterization mode, separating the light emitted from the light source 200 into a probe light Lpr and a reference light of different polarizations from each other and advancing the same, and then combining optical paths of the probe light Lpr and the reference light, an objective lens 400 disposed on the optical path of the probe light Lpr to focus the probe light Lpr, and movable along an optical path direction of the probe light Lpr so as to vary a focal position of the probe light Lpr along a depth direction of a holographic data storage medium 401, a 4F system 500 positioned on the optical path of the probe light Lpr between the objective lens 400 and the holographic data storage medium 401 to relay the probe light Lpr toward the holographic data storage medium 401, and a scattering lens 610 disposed on the optical path of the probe light Lpr between the objective lens 400 and the 4F system 500 to scatter the probe light Lpr focused by the objective lens 400, a beam blocking part 620 disposed on the optical path of the probe light Lpr between the light source 200 and the objective lens 400 to block the probe light Lpr in the playback mode, an optical modulator 630 for, in the playback mode, receiving the reference light Lref transferred through the optical path-forming optical system 300, modulating the reference light Lref to emit a playback light Lpl, and emitting the playback light Lpl along the optical path of the probe light Lpr in a direction opposite an irradiation direction of the probe light Lpr, a photodetector 640 disposed at a position adjacent to the optical path of the probe light Lpr to detect the playback light Lpl, and a beam splitter 650 disposed on the optical path of the probe light Lpr in front of the objective lens 400 with reference to an advancing direction of the probe light Lpr to pass the probe light Lpr entering the objective lens 400, while transferring the playback light Lpl that has passed through the objective lens 400 to the photodetector 640.

The light source 200 may be a laser diode that emits a laser beam pulsed at 532 nm.

The optical path-forming optical system 300 includes a first optical path converter 310 for splitting the beam emitted from the light source 200 into a probe light and a reference light, a filter part 320 for filtering the probe light Lpr and the reference light split from the first optical path converter 310, first and second polarization parts 330 and 340 for converting polarized lights of the probe light Lpr and the reference light passing the filter part 320 so as to include two mutually orthogonally polarized lights, a conversion mirror 350 for changing the optical path of the probe light Lpr passing the first polarization part 330 to a direction intersecting with the optical path of the reference light Lref, and a second optical path converter 360 disposed at an intersection of the probe light Lpr whose optical path is changed by the conversion mirror 350 and the reference light Lref, to change optical path so that the probe light Lpr and the reference light Lref are interfered with each other so as to be incident on the holographic data storage medium 401. In the above example, the holographic data storage medium 401 is preferably a scientific complementary metal oxide semiconductor (sCMOS).

The first optical path converter 310 is configured to split the beam emitted from the light source 200 into the probe light Lpr and the reference light Lref, in which the probe light Lpr is split to a direction orthogonal to the optical path of the reference light Lref. A beam splitter may be applied.

In an example, the optical path-forming optical system 300 additionally includes an adjusting part 311 disposed behind the first optical path converter 310 to adjust the optical path of the probe light Lpr so that the probe light Lpr emitted from the first optical path converter 310 is irradiated in a direction parallel to the reference light Lref. The adjusting part 311 is disposed on the optical path of the probe light Lpr and includes a path delay part 312 for guiding the probe light Lpr in a direction opposite the irradiation direction of the probe light Lpr, and a reflection mirror 313 disposed on the optical path of the probe light Lpr that has passed through the path delay part 312 to reflect the probe light Lpr in a direction parallel to the irradiation direction of the reference light Lref.

The filter part 320 includes a first filter member 321 disposed on the optical path of the probe light Lpr reflected through the reflection mirror 313, and a second filter member 322 disposed on the optical path of the reference light Lref split from the first optical path converter 310.

The first and second filter members 321 and 322 each include a single mode optical fiber through which the probe light Lpr and the reference light Lref pass, and the probe light Lpr and the reference light Lref are spatially filtered through the single mode optical fibers.

The first polarization part 330 includes a first focusing lens 331 disposed on the optical path of the probe light Lpr behind the first filter member 321 with reference to the irradiation direction of the probe light Lpr, and a first polarization conversion element 332 disposed on the optical path of the probe light Lpr behind the first focusing lens 331.

A lens having a focal distance of 30 mm is applied as the first focusing lens 331, and a half wave plate is applied as the first polarization conversion element 332. The first polarization conversion element 332 changes the polarization state of the probe light Lpr that has passed through the first focusing lens 331. Since the first polarization conversion element 332 is a wave plate generally used in the art, detailed description thereof will be omitted.

Further, the first linear polarizer 333 is disposed on the optical path of the probe light Lpr behind the first polarization conversion element 332 with reference to the irradiation direction of the probe light Lpr. The first linear polarizer 333 converts the probe light Lpr that has passed through the first polarization conversion element 332 into linearly polarized light. Since the first linear polarizer 333 is a linear polarizer generally used in the art, detailed description thereof is omitted.

The second polarization part 340 includes a second focusing lens 341 disposed on the optical path of the reference light Lref behind the second filter member 322 with reference to the irradiation direction of the reference light Lref, and a second polarization conversion element 342 disposed on the optical path of the reference light Lref behind the second focusing lens 341.

A lens having a focal distance of 200 mm is applied as the second focusing lens 341, and a half wave plate is applied as the second polarization conversion element 342. The second polarization conversion element 342 changes the polarization state of the reference light Lref passed through the second focusing lens 341 to be different from the polarization state of the probe light Lpr. Since the second polarization conversion element 342 is a wave plate generally used in the art, detailed description thereof will be omitted.

The second linear polarizer 343 is disposed on the optical path of the reference light Lref behind the second polarization conversion element 342 with reference to the irradiation direction of the reference light Lref. The second linear polarizer 343 converts the reference light Lref that has passed through the second polarization conversion element 342 into linearly polarized light. Since the second linear polarizer 343 is a linear polarizer generally used in the art, detailed description thereof is omitted.

The conversion mirror 350 is disposed on the optical path of the probe light Lpr behind the first linear polarizer 333 with reference to the irradiation direction of the probe light Lpr to reflect the probe light Lpr so that the probe light Lpr intersects with the reference light Lref. In an example, it is preferable that the conversion mirror 350 reflects the probe light Lpr so that the probe light Lpr intersects in a direction orthogonal to the reference light Lref.

The second optical path converter 360 is disposed at an intersection of the probe light Lpr and the reference light Lref to cause the probe light Lpr and the reference light Lref to be incident on the holographic data storage medium 401 so that the reference light Lref is interfered with the probe light Lpr. In an example, the second optical path converter 360 in the playback mode reflects the incoming reference light Lref toward the optical modulator 630, while passing the playback light Lpl emitted from the optical modulator 630.

The objective lens 400 is disposed on the optical path of the probe light Lpr between the conversion mirror 350 and the first linear polarizer 333 to focus the probe light Lpr that has passed through the first linear polarizer 333. In an example, the objective lens 400 preferably has 10 times magnification and a numerical aperture of 0.25. The objective lens 400 is movably disposed so as to move along the optical path of the probe light Lpr, and is driven by a driving part (not shown).

A 4F system 500 includes a plurality of third focusing lenses 501 disposed on the optical path of the probe light Lpr between the objective lens 400 and the conversion mirror 350, and a transmissive plate 502 being disposed among the plurality of third focusing lenses 501 and having an aperture formed on the optical axis of the probe light Lpr to permit the probe light Lpr to pass therethrough. In an example, it is preferable that the aperture has an inner diameter of 3 mm. Since the 4F system 500 is a generally used system in the art, detailed description thereof will be omitted.

The scattering lens 610 is an optical conjugation supported scattering lens that operates as a variable focusing lens. The scattering lens 610 is disposed on the optical path of the probe light Lpr between the objective lens 400 and the 4F system 500 to scatter the probe light Lpr focused through the objective lens 400. Although not shown, the scattering lens 610 includes a slide plate formed of a light-transmitting material, and a scattering layer formed by applying scattering particles onto the surface of the slide plate so as to scatter light passing through the slide plate. In an example, it is preferable that the scattering particles include zinc oxide (ZnO), and the oxide layer is formed with a thickness of 5.6 µm.

Meanwhile, the scattering lens 610 is not limited to the specific example provided above, but may be any lens that is capable of scattering the probe light Lpr focused through the objective lens 400. A third linear polarizer 611 is disposed behind the scattering lens 610 to convert the probe light Lpr passed through the scattering lens 610 into linearly polarized light.

The beam blocking part 620 is disposed on the optical path of the probe light Lpr between the first optical path converter 310 and the adjusting part 311, and passes the probe light Lpr in the characterization mode and blocks the probe light Lpr in the playback mode.

The optical modulator 630 is disposed at a position adjacent to the second optical path converter 360 and in the playback mode, is implemented as a spatial light modulator that receives the reference light Lref transmitted through the second optical path converter 360, modulates the reference light Lref to emit the playback light Lpl, and emits the playback light Lpl in a direction opposite the irradiation direction of the probe light Lpr along the optical path of the probe light Lpr. The optical modulator emits a conjugated wavefront through the playback light Lpl to generate one spot, or a plurality of spots through the scattering lens 610.

The photodetector 640 is disposed between the first linear polarizer 333 and the objective lens 400 and is spaced apart from the optical path of the probe light Lpr. The photodetector 640 may preferably be a charge-coupled device (CCD). In an example, a fourth focusing lens 641 may be disposed between the photodetector 640 and the beam splitter 650. The fourth focusing lens 641 is preferably a lens having a focal distance of 500 mm.

The beam splitter 650 is disposed on the optical path of the probe light Lpr between the first linear polarizer 333 and the objective lens 400, and passes the probe light Lpr incident on the objective lens 400, while transferring the playback light Lpl that has passed through the objective lens 400 to the photodetector 640. The beam splitter 650 is a beam splitter generally used in the art, and detailed description thereof will be omitted.

The characterization mode using the holographic characterization and playback apparatus 100 configured as described above, that is, the characterization step will be described in detail.

Light, i.e., a laser beam having a wavelength of 532 nm, a pulse width of 5 ns, a repetition rate of 2 kHz, and a coherence length of 7 mm is emitted from the light source 200, and the laser beam is split through the first optical path converter 310 into the probe light Lpr and the reference light Lref. In an example, the probe light Lpr is focused through the objective lens 400, and scattered through the scattering lens 610 and transmitted. The transmitted probe light Lpr is stored in the holographic data storage medium 401 through the 4F system 500. In an example, the phase map of the probe light Lpr is calculated with off-axis holography method by a computer connected to the holographic data storage medium 401 and stored.

In an example, the characterization step involves characterization of a random wavefront originating from a reference spot behind the scattering lens 610, which is repeatedly performed at several positions of the reference spot along the optical axis of the probe light Lpr, while moving the objective lens 400.

In the playback mode, the probe beam emitted from the first optical path converter 310 to the adjusting part 311 is blocked at the beam blocking part 620, and the reference light Lref falls incident on the optical modulator 630 by the second optical path converter 160. The optical modulator 630 displays a conjugated wavefront to generate one spot, or a plurality of spots through the scattering lens 610. The playback light Lpl emitted from the optical modulator 630 is emitted along the optical path of the probe light Lpr in a direction opposite the irradiation direction of the probe light Lpr. The playback light Lpl is focused through the scattering lens 610 by time-reversal symmetry. The focal plane of the scattering lens 610 is imaged at the photodetector 640 by the objective lens 400 and the beam splitter 650 for visual observation of the focal spot.

According to the present disclosure, variable focusing is provided in which, in a characterization mode, a plurality of wavefronts at different axial locations of a reference spot are captured and the captured wavefronts are optically positioned on the surface of the scattering lens 610 through the 4F system 500, and in the playback mode, a phase-conjugated copy of the recorded wavefront is calculated and displayed on the optical modulator 630 and then the playback light, which is the reference light reflected from the optical modulator 630, is focused through the scattering lens 610 by time-reversal symmetry and imaged onto the CMOS camera (i.e., holographic data storage medium 401) so that the focal plane of the scattering lens 610 shows a focus. The scattering lens 610 is characterized for a focal distance that ranges from 22 mm to 51 mm by the movement of the objective lens 400, and then wavefront is captured to create a focal spot at each focal distance, and a focal spot having a variable focal length of 22 nm to 51 mm is provided. According to an exemplary embodiment, the captured wavefront and a linear phase gradient are combined to laterally shift the focus, and a plurality of focuses at different focal distances are generated by adding a plurality of gradient maps to a single phase-conjugate wavefront, and displayed by the optical modulator 630.

In an example, the focusing accuracy of the apparatus may be defined by the peak to background ratio (PBR) of the reconstructed focal spot. In contrast to the conventional focusing schemes, the holographic characterization and playback apparatus 100 according to the present disclosure cannot separate the background from the interference measurement approach, which is attributable to the partial measurement of the wavefront emerging from the scattering lens 610.

If the input field phase is only controlled only in a time-reversal process, then PBR has the relationship as shown in Mathematical Equation 1 below for the number of controllable input modes.

$$PBR_1 = \frac{\pi}{4}N \quad \text{[Mathematical Equation 1]}$$

where $PBR_1$ is a single optical mode (i.e., focal spot) that is reconstructed through a time-reversal process. Further, N is the number of controllable input modes and is a value up to 4000. From Mathematical Equation 1, the theoretical value of $PBR_1$ is up to 31,000, and the actual $PBR_1$ by the digital auto-alignment method has a value of 8 to 25 percent of the theoretical $PBR_1$.

Meanwhile, when generating a light pattern made up of a plurality of optical modes, a plurality of wavefronts that independently optimize each optical mode are added behind the scattering lens 610. Thus, 1/K (number of optical modes) energy from the input side contributes to the light intensity in each light mode within the desired light pattern. The PBR of the optical pattern is obtained by Mathematical Equation 2 below.

$$PBR_K = \frac{PBR_1}{K} = \frac{\pi}{4}\frac{N}{K} \quad \text{[Mathematical Equation 2]}$$

where N is the number of controllable input modes, which is a value up to 4000, and K is the number of optical modes.

Figure 3A:
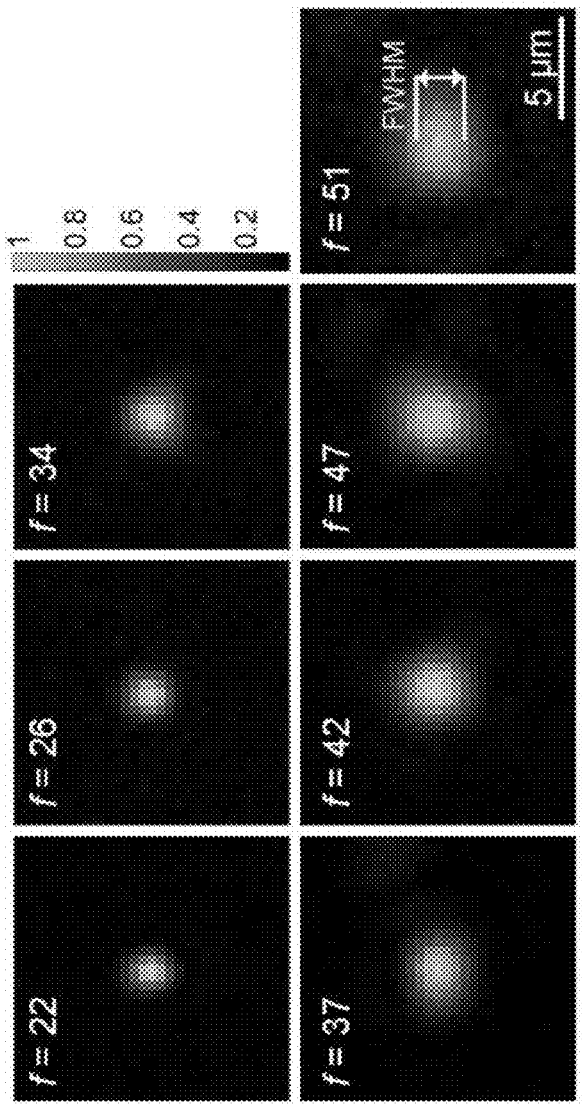
FIG. 3A shows focal spot images at different focal distances of a scattering lens of a holographic characterization and playback apparatus according to exemplary embodiments.
Figure 3B:
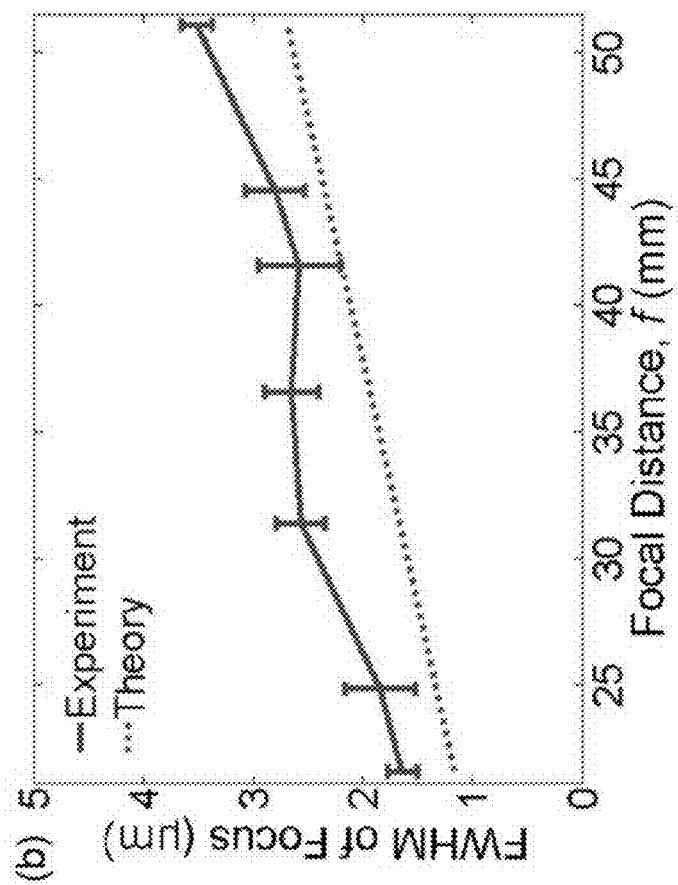
FIG. 3B is a graph of theoretical data and experimental data on distribution of the focal spots reconstructed at different focal distances of a scattering lens and Full Width at Half Maximum (FWHM) of a holographic characterization and playback apparatus according to exemplary embodiments.

In the holographic characterization and playback apparatus 100 according to exemplary embodiments, the scattering lens 610 is characterized for a focal distance ranging from 22 mm to 51 mm. The holographic characterization and playback apparatus 100 then plays back the wavefronts respectively captured to create focal spot at respective focal distances, through the optical modulator 630. Distribution of the reconstructed focal spot at different focal distances and the full width at half maximum (FWHM) are shown in FIGS. 3A and 3B.

FWHM having a range of 1.5 μm to 3.5 μm corresponds to a numerical aperture of 0.08 to 0.18. In an example, the aperture size is fixed, and the numerical aperture is inversely proportional to the focal distance. The focal spot size increases in proportion to the increase of the focal distance. The theoretical formula is given by Mathematical Equation 3 below.

$$\text{FWHM of the focal spot} = 0.51\lambda/NA = 0.51\lambda/\sin[\tan^{-1}(d/2f)] \quad \text{[Mathematical Equation 3]}$$

where d is the aperture size of the scattering lens 610 (10 mm with a 1.25× magnification of the 4F system 500), NA is the numerical aperture of the scattering lens 610, λ is the wavelength of the light, and f is the focal distance. The error of the theoretical value is attributable to the misalignment of the lens and the marginal distortion of the reference wavefront. When it is assumed that the alignment is excellent, $PBR_1$ has a range of 2500 to 8000.

Figure 4A:
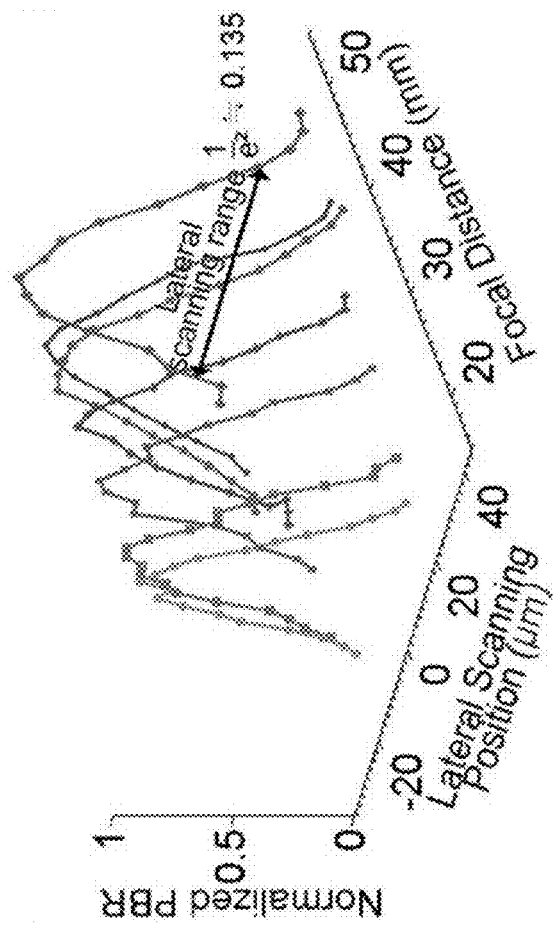
FIG. 4A is a graph of normalized peak intensity of a focal spot at different lateral scanning positions and focal distances of a scattering lens of a holographic characterization and playback apparatus according to exemplary embodiments.

By combining the captured wavefront with a liner phase gradient, the focus can be moved in the transverse direction, i.e., in the longitudinal direction of the optical axis. In FIG. 4A, the normalized peak intensities of the focal spots at different transverse scanning positions and focal distances are shown.

Figure 4B:
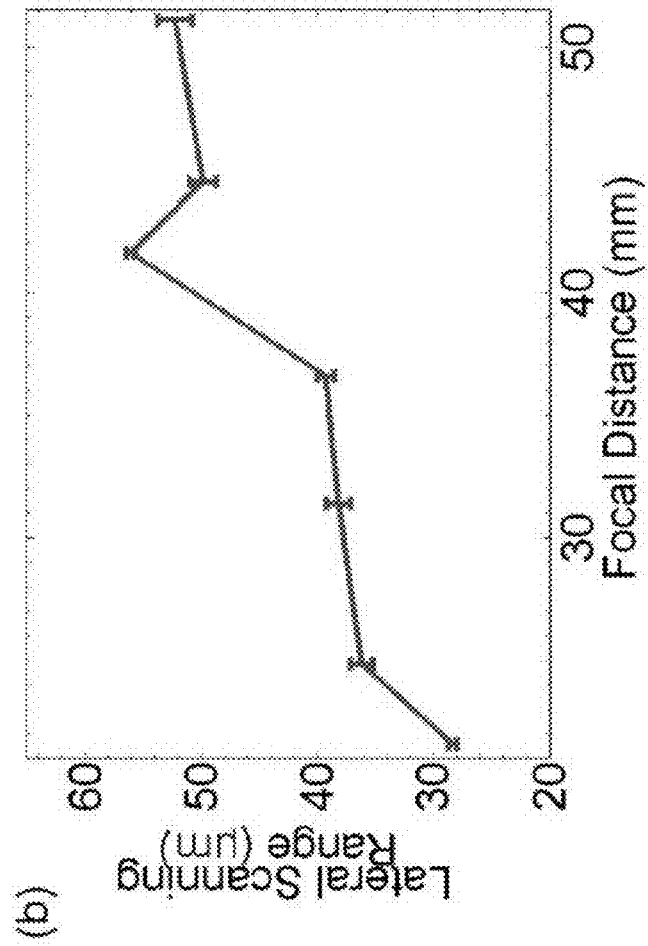
FIG. 4B is a graph of theoretical and experimental full width at a profile of $1/e^2$ intensity according to different focal distances of a scattering lens of a holographic characterization and playback apparatus according to exemplary embodiments.

Referring to FIG. 4B, the lateral scanning range obtained as a full width at $1/e^2$ may be 28 to 56 microns. Since the scanning range of the angle is not affected by the focal distance, the scanning range is increased in proportion to the focal distance.

Figure 5A:
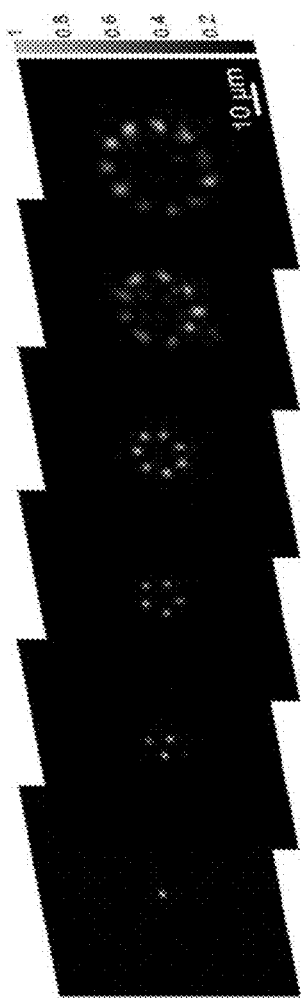
FIG. 5A illustrates focal images in a set focal distance range of a scattering lens of a holographic characterization and playback apparatus according to exemplary embodiments.
Figure 5B:
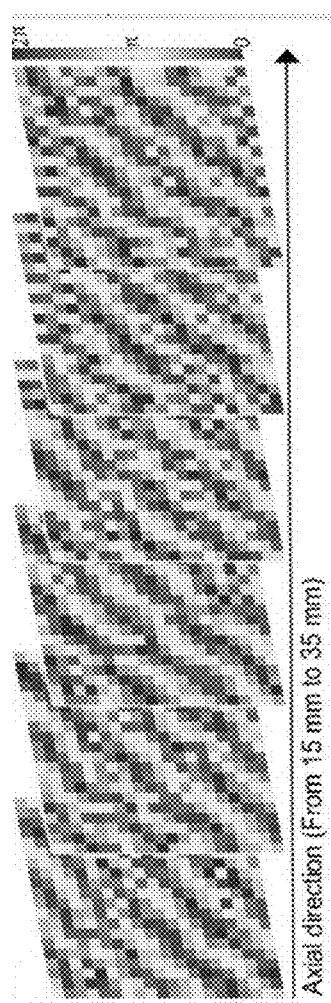
FIG. 5B illustrates a phase map for each of set focal distances of a scattering lens of a holographic characterization and playback apparatus according to exemplary embodiments.

Meanwhile, referring to FIGS. 5A and 5B, an arbitrary optical patterning based on the superposition principle will be described as follows. FIGS. 5A and 5B illustrate that a wavefront at each focal distance is recorded while varying the focal distance at intervals of 5 mm in a range of 15 mm to 35 mm, and then a phase map for a plurality of focal points is synthesized and separately played back. FIG. 5A shows an image of focus at each focal distance, with each image being normalized to peak intensity. FIG. 5B shows a phase map for each focal distance, in which the phase map is represented by a 20×20 pixel image.

By adding a plurality of phase gradient maps to a single phase conjugate wavefront as shown in FIG. 5A, a plurality of focal points are created at different focal distances, and wavefronts are synthesized as shown in FIG. 5B.

Through the reduction of imperfect wavefront modulation in the short distance correlation, PBR is reduced by 20 times, as the number of reconstructed focal spots increases from 1 to 11.

The maximum number of practically available optical modes depends on the application. For example, if a scattering lens 610 is used for selective optogenetic stimulations, PBR 100 is required for 5-fold modulation of maximal neuronal response. In this case, the maximum number of possible optical modes that can be optimized through the scattering lens 610 exceeds 20.

Figure 6:
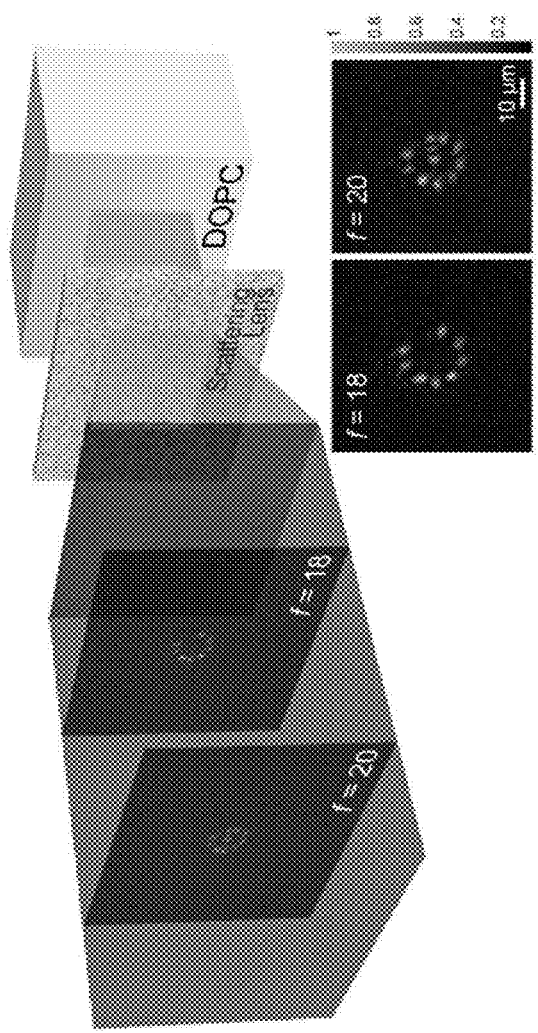
FIG. 6 illustrates an arbitrary 3D patterning simultaneously generated through a scattering lens of a holographic characterization and playback apparatus according to exemplary embodiments.

FIG. 6 is a diagram illustrating the simultaneous generation of an arbitrary 3D patterning through the scattering lens 610. The phase maps 'C' and 'G' are synthesized based on two wavefronts captured at two different focal distances (18 mm and 20 mm), respectively. The two phase maps are then superimposed and displayed on the optical modulator 630. It can be seen that these patterns 'C' and 'G' are generated 18 mm and 20 mm behind the scattering lens 610 through the modified objective lens.

That is, in the present disclosure, the scattering lens 610 may operate as a variable focusing lens.

The scattering lens 610 having the aperture of a width of 10×10 square millimeters provides a microscale focal spot of a variable focal length of 22 mm to 55 mm. The short distance correlation of the scattering lens 610 enables the lateral movement of the spot through a simple deformation of the characterized wavefront. Using a digital wavefront shaper, a plurality of wavefronts can be superimposed to create an arbitrary light pattern in a three-dimensional space. The scattering lens 610 is immune to lens aberration. Thus, as the lens aperture increases, the scattering lens 610 provides more fluidity. Theoretically, a larger aperture can be achieved by a higher magnification of the relay system between the digital optical phase conjugation plane and the scattering lens.

According to the present disclosure, at a peak intensity of $1/e^2$ and without lateral scanning, the lateral focusing range may be approximately 25 µm to 50 µm. However, $PBR_1$ corresponding to the peak intensity is 2500 to 8000, and even with the application having a reduction ratio of 1/100, this $PBR_1$ is high enough. Thus, the available field of view (FOV) of the scattering lens 610 can be extended to 40 µm to 100 µm. By making an overall short distance correlation with improved arrangement between the image plane of the optical modulator 630 and the scattering lens 610, and by increasing the total number of characterization points on the horizontal plane, the lateral scanning range can be enhanced.

According to the present disclosure, the scattering lens 610 provides good fluidity for variable optical focusing and optical patterning, and can be used for various optical applications. For example, the present disclosure can be used as an optical illumination system for fluorescence microscopy techniques, and is excellent for good definition optical focusing through thick specimens such as tissues. The present disclosure can be applied in imaging applications in which the arrangement of focal spots due to fast scanning from galvo mirrors and digital micromirror devices can greatly improve the imaging speed. In addition, the present disclosure has the advantage that the field of view is extended through the scattering lens 610.

The description of the disclosed embodiments is provided to enable those skilled in the art to make or use the invention. Various modifications to these embodiments will be readily apparent to those skilled in the art, and the generic principles defined herein may be applied to other embodiments without departing from the scope of the invention. Thus, the invention is not to be limited to the embodiments shown herein but is to be interpreted within the broadest scope consistent with the principles and novel features presented herein.

Further, the foregoing exemplary embodiments and advantages are merely exemplary and are not to be construed as limiting the exemplary embodiments. The present teaching can be readily applied to other types of apparatuses. Also, the description of the exemplary embodiments of the present inventive concept is intended to be illustrative, and not to limit the scope of the claims.

What is claimed is:

1. A holographic characterization and playback apparatus, comprising:
   a light source for emitting light;
   an optical path-forming optical system for, in the characterization mode, separating the light emitted from the light source into a probe light and a reference light of different polarizations from each other and advancing the same, and then combining optical paths of the probe light and the reference light;
   an objective lens disposed on the optical path of the probe light to focus the probe light, and movable along an optical path direction of the probe light so as to vary a focal position of the probe light along a depth direction of a holographic data storage medium;
   a scattering lens disposed on the optical path of the probe light between the objective lens and the holographic data storage medium to scatter the probe light focused by the objective lens;
   a beam blocking part disposed on the optical path of the probe light between the light source and the objective lens to block the probe light in a playback mode;
   an optical modulator for, in the playback mode, receiving the reference light transferred through the optical path-forming optical system, modulating the reference light to emit a playback light, and emitting the playback light along the optical path of the probe light in a direction opposite an irradiation direction of the probe light;
   a photodetector disposed at a position adjacent to the optical path of the probe light to detect the playback light; and
   a beam splitter disposed on the optical path of the probe light in front of the objective lens with reference to an advancing direction of the probe light to pass the probe light entering the objective lens, while transferring the playback light that has passed through the objective lens to the photodetector.

2. The holographic characterization and playback apparatus of claim 1, wherein the scattering lens comprises a slide plate formed of a light transmitting material, and a scattering layer formed by applying scattering particles onto a surface of the slide plate so as to scatter light passing through the slide plate.

3. The holographic characterization and playback apparatus of claim 2, wherein the scattering particles comprise zinc oxide.

4. The holographic characterization and playback apparatus of claim 3, wherein the optical path-forming optical system comprises:
a first optical path converter for splitting the light emitted from the light source into the probe light and the reference light;
first and second polarization parts respectively disposed on the optical paths of the probe light and the reference light separated from the first optical path converter, and converting polarized lights of the probe light and the reference light so as to include two mutually orthogonally polarized lights;
a conversion mirror disposed on the optical path of the probe light that has passed through the first polarization part to change the optical path of the probe light to a direction intersecting with the optical path of the reference light; and
a second optical path converter disposed at an intersection of the probe light whose optical path is changed by the conversion mirror and the reference light, to change optical path so that the probe light and the reference light are interfered with each other so as to be incident on the holographic data storage medium.

5. The holographic characterization and playback apparatus of claim 4, wherein the optical path-forming optical system further comprises a first filter member disposed on the optical path of the probe light between the first optical path converter and the first polarization part to filter the probe light.

6. The holographic characterization and playback apparatus of claim 4, wherein the optical path-forming optical system further comprises a second filter member disposed on the optical path of the reference light between the first optical path converter and the second polarization part to filter the reference light.

7. The holographic characterization and playback apparatus of claim 4, wherein the first polarization part comprises a first focusing lens disposed on the optical path of the probe light behind the first optical path converter with reference to the irradiation direction of the probe light, and a first polarization conversion element disposed on the optical path of the probe light behind the first focusing lens to change a polarization state of the probe light that has passed through the first focusing lens.

8. The holographic characterization and playback apparatus of claim 7, wherein the first polarization part further comprises a first linear polarizer disposed on the optical path of the probe light behind the first polarization conversion element with reference to the irradiation direction of the probe light to convert the probe light that has passed through the first polarization conversion element into linearly polarized light.

9. The holographic characterization and playback apparatus of claim 7, wherein the second polarization part comprises a second focusing lens disposed on the optical path of the reference light behind the first optical path converter with reference to the irradiation direction of the reference light, and a second polarization conversion element disposed on the optical path of the reference light behind the second focusing lens to change the polarization state of the reference light that has passed through the second focusing lens.

10. The holographic characterization and playback apparatus of claim 9, wherein the second polarization part further comprises a second linear polarizer disposed on the optical path of the reference light behind the second polarization conversion element with reference to the irradiation direction of the reference light to convert the reference light that has passed through the second polarization conversion element into linearly polarized light.

11. The holographic characterization and playback apparatus of claim 9, wherein the first and second focusing lenses are formed with different focal distances from each other.

12. The holographic characterization and playback apparatus of claim 11, wherein the first focusing lens is formed with a focal distance of 30 mm, and the second focusing lens is formed with a focal distance of 200 mm.

13. The holographic characterization and playback apparatus of claim 3, further comprising a third linear polarizer disposed on the optical path of the probe light between the scattering lens and a 4F system to convert the probe light that has passed through the scattering lens into linearly polarized light.

14. The holographic characterization and playback apparatus of claim 4, wherein the second optical path converter in a playback mode reflects the reference light incident from the second polarization part toward the optical modulator, while passing the playback light so that the playback light emitted from the optical modulator is emitted along the optical path of the probe light.

15. The holographic characterization and playback apparatus of claim 1, further comprising a 4F system positioned on the optical path of the probe light between the scattering lens and the holographic data storage medium to relay the probe light toward the holographic data storage medium.

16. The holographic characterization and playback apparatus of claim 15, wherein the 4F system comprises a plurality of third focusing lenses spaced apart from one another along the optical path of the probe light, and a transmissive plate disposed on the optical path of the probe light among the plurality of third focusing lenses, wherein the transmissive plate comprises an aperture formed on an optical axis of the probe light so that the probe light can pass through.

* * * * *